United States Patent
Saegusa

(10) Patent No.: US 7,799,574 B2
(45) Date of Patent: Sep. 21, 2010

(54) DISPENSING APPARATUS AND IN-DUCT BUBBLE PRESENCE DETERMINING METHOD IN THE SAME

(75) Inventor: Isao Saegusa, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 176 days.

(21) Appl. No.: 12/186,077

(22) Filed: Aug. 5, 2008

(65) Prior Publication Data

US 2008/0289437 A1 Nov. 27, 2008

Related U.S. Application Data

(63) Continuation of application No. PCT/JP2007/057469, filed on Apr. 3, 2007.

(30) Foreign Application Priority Data

Apr. 6, 2006 (JP) ............................. 2006-105301

(51) Int. Cl.
- *G01N 7/00* (2006.01)
- *G01N 35/08* (2006.01)
- *G01N 1/14* (2006.01)
- *B01L 1/02* (2006.01)

(52) U.S. Cl. .................. 436/148; 436/180; 436/44; 436/55; 422/100; 422/68.1; 422/105; 422/106

(58) Field of Classification Search .............. 422/100, 422/63, 68.1, 105–106; 436/180, 43, 55, 436/148

See application file for complete search history.

(56) References Cited

U.S. PATENT DOCUMENTS

| | | | |
|---|---|---|---|
| 5,463,895 A * | 11/1995 | Brentz | 73/61.71 |
| 5,488,854 A | 2/1996 | Kawanabe et al. | |
| 5,540,081 A * | 7/1996 | Takeda et al. | 73/37 |
| 6,022,747 A * | 2/2000 | Gherson et al. | 436/69 |
| 6,121,049 A * | 9/2000 | Dorenkott et al. | 436/50 |
| 6,370,942 B1 * | 4/2002 | Dunfee et al. | 73/37 |
| 6,641,545 B1 * | 11/2003 | Colin et al. | 600/573 |
| 7,477,997 B2 * | 1/2009 | Kaplit | 702/55 |
| 2001/0016177 A1 * | 8/2001 | Pelc et al. | 422/100 |
| 2003/0211620 A1 * | 11/2003 | LaBudde et al. | 436/50 |
| 2004/0048393 A1 * | 3/2004 | Colin et al. | 436/180 |
| 2007/0143063 A1 * | 6/2007 | Kaplit | 702/140 |
| 2009/0117010 A1 * | 5/2009 | Bjorson et al. | 422/100 |

FOREIGN PATENT DOCUMENTS

| | | |
|---|---|---|
| JP | 5-249124 | 9/1993 |
| JP | 10-227799 | 8/1998 |
| JP | 2003-254982 | 9/2003 |

* cited by examiner

*Primary Examiner*—Brian R Gordon
(74) *Attorney, Agent, or Firm*—Townsend and Townsend and Crew LLP.

(57) ABSTRACT

A dispensing apparatus performs dispensing by filling a duct to which a dispensing nozzle is connected with a liquid, making the liquid move in the duct to absorb a liquid sample including a specimen or a reagent through the dispensing nozzle, and discharging the absorbed liquid sample; and an in-duct bubble presence determining method in the dispensing apparatus. The presence determining method includes discharging the liquid in the duct from the dispensing nozzle and detecting a transition of a pressure in the duct; calculating the number of mountain pulses in a pressure transition waveform based on the detected pressure transition; and determining a presence of a bubble in the duct based on the calculated number of mountain pulses.

4 Claims, 5 Drawing Sheets

DISPENSING APPARATUS AND IN-DUCT BUBBLE PRESENCE DETERMINING METHOD IN THE SAME

CROSS-REFERENCE TO RELATED APPLICATIONS

This application is a continuation of PCT international application Ser. No. PCT/JP2007/57469 filed Apr. 3, 2007 which designates the United States, incorporated herein by reference, and which claims the benefit of priority from Japanese Patent Application No. 2006-105301 filed Apr. 6, 2006, incorporated herein by reference.

BACKGROUND OF THE INVENTION

1. Field of the Invention

The present invention relates to a dispensing apparatus and an in-duct bubble presence determining method in the dispensing apparatus.

2. Description of the Related Art

Conventionally, a dispensing apparatus which is used in dispensing a liquid sample including a specimen or a reagent in an analyzing device absorbs and discharges a liquid, for example cleansing water, in a duct by using a supplying/discharging pump, so that the liquid sample is absorbed through a dispensing nozzle connected to the duct and the absorbed liquid sample is discharged and dispensed to a predetermined position. On this occasion, when a bubble is mixed into the cleansing water, the dispensing apparatus comes to have a lower precision in dispensing the liquid sample due to the bubble. For this reason, the dispensing apparatus fills the duct with deaerated cleansing water.

However, when parts connected to the duct are detached and attached for maintenance and the like, there is a case where a little bubble gets mixed in the duct. In this case, there is a possibility that the dispensing precision in the dispensing apparatus deteriorates without someone's knowledge since the bubble cannot be found easily.

In response to this, a dispensing apparatus having a function of detecting the presence of a bubble in a duct has been proposed (see Japanese Patent Application Laid-Open No. 2003-254982, for example).

SUMMARY OF THE INVENTION

An in-duct bubble presence determining method according to an aspect of the present invention is performed in a dispensing apparatus which performs dispensing by filling a duct to which a dispensing nozzle is connected with a liquid, making the liquid move in the duct to absorb a liquid sample including one of a specimen and a reagent through the dispensing nozzle, and discharging the absorbed liquid sample. The method includes discharging the liquid in the duct from the dispensing nozzle and detecting a transition of a pressure in the duct; calculating a number of mountain pulses in a pressure transition waveform based on the detected pressure transition; and determining a presence of a bubble the liquid filling the duct based on the calculated number of mountain pulses.

A dispensing apparatus according to another aspect of the present invention performs dispensing by filling a duct to which a dispensing nozzle is connected with a liquid, making the liquid move in the duct to absorb a liquid sample including one of a specimen and a reagent through the dispensing nozzle, and discharging the absorbed liquid sample. The dispensing apparatus includes a pressure sensor that detects a transition of a pressure in the duct; and a determining unit that discharges the liquid in the duct from the dispensing nozzle, calculates a number of mountain pulses in a pressure transition waveform based on the pressure transition in the duct detected by the pressure sensor, and determines a presence of a bubble the liquid filling the duct based on the calculated number of mountain pulses.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
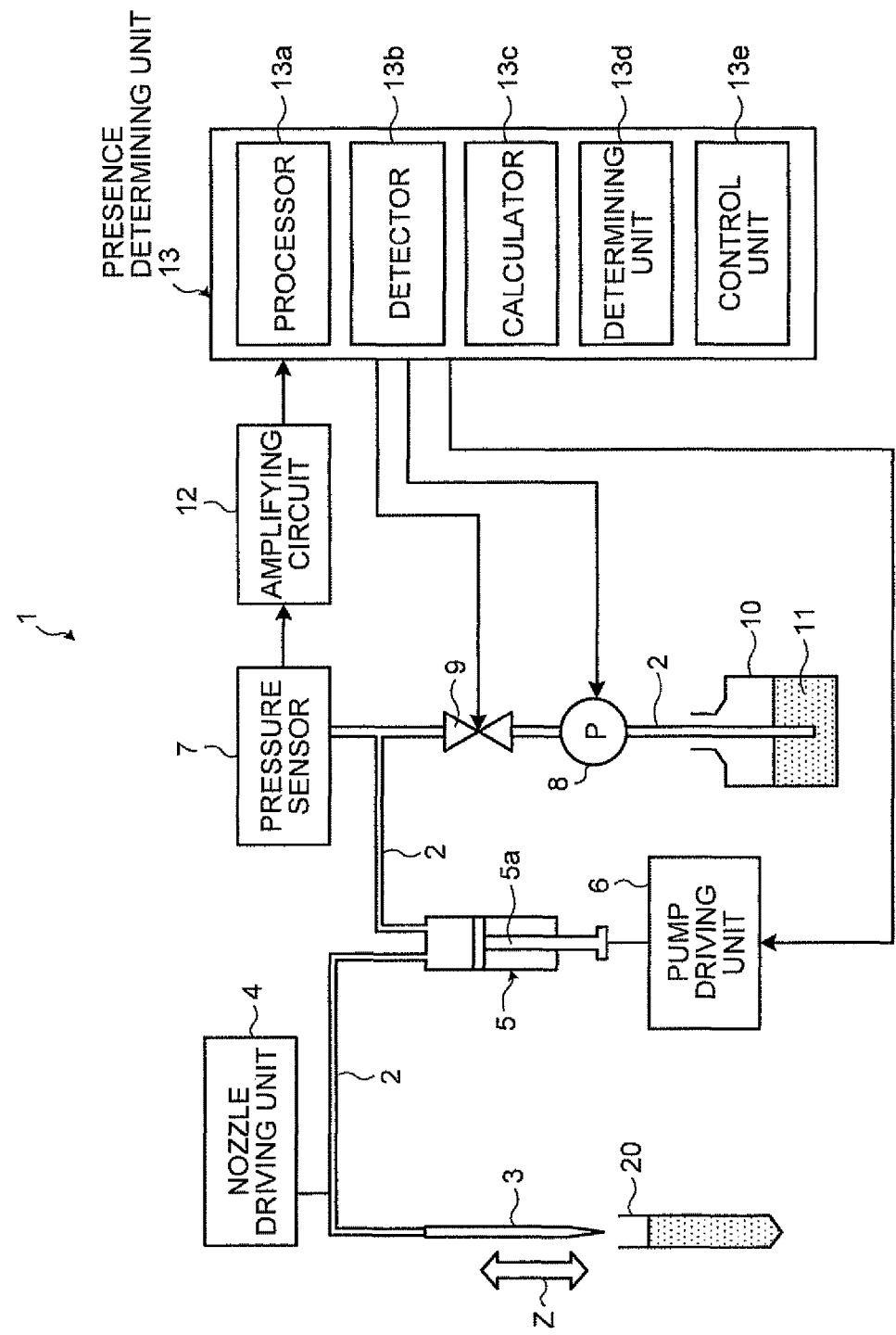
FIG. 1 is a block diagram showing a structure of a dispensing apparatus according to the present invention.
Figure 2:
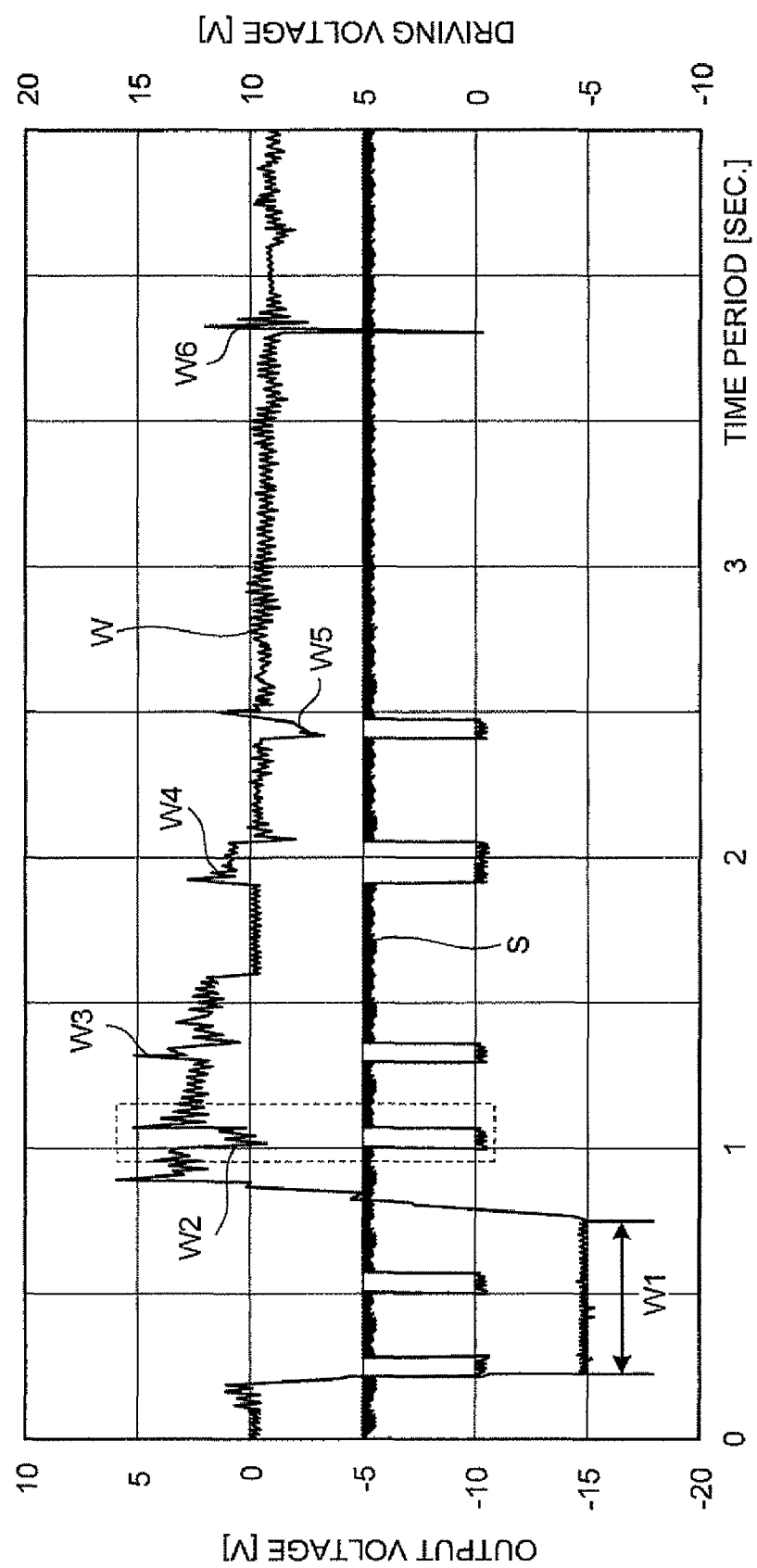
FIG. 2 is a pressure transition waveform showing, based on voltages output by a pressure sensor, a transition of an in-duct pressure at a time of dispensing a specimen from a probe.

Exemplary embodiments of a dispensing apparatus and an in-duct bubble presence determining method in the dispensing apparatus according to the present invention will be explained in detail below with reference to the accompanying drawings. FIG. 1 is a block diagram showing a structure of a dispensing apparatus according to the present invention. FIG. 2 is a pressure transition waveform showing, based on voltages output by a pressure sensor, a transition of an in-duct pressure at a time of dispensing a specimen through a probe 3. As shown in FIG. 1, a dispensing apparatus 1 includes the probe 3, a dispensing pump 5, a pressure sensor 7, a cleansing water pump 8, an amplifying circuit 12, and a presence determining unit 13, and is used independently or by being incorporated in an analyzing device.

The probe 3 is connected to the dispensing pump 5, the pressure sensor 7, and the cleansing water pump 8 by a duct 2. The probe 3 is moved by a nozzle driving unit 4 in a vertical direction shown by an arrow Z in FIG. 1, absorbs a specimen from a sample cup 20 sequentially conveyed under the probe 3, and discharges the specimen into a reaction vessel to dispense the specimen.

The dispensing pump 5 is a syringe pump which absorbs the specimen in the sample cup 20 into the probe 3 and discharges the absorbed specimen into the reaction vessel which is conveyed by following the sample cup 20, and a piston 5a is reciprocated by a pump driving unit 6.

The pressure sensor 7 detects a pressure in the duct 2 and outputs as a pressure signal (analogue) to the amplifying circuit 12.

The cleansing water pump 8 absorbs deaerated cleansing water 11 retained in a tank 10 and transports with pressure into the duct 2 via an electromagnetic valve 9 provided between the pressure sensor 7 and the cleansing water pump 8. On this occasion, the electromagnetic valve 9 is switched, based on a control signal from a detector 13b, to "open" when the absorbed cleansing water 11 is supposed to be transported with pressure into the duct 2, and switched to "close" when the liquid sample is supposed to be absorbed and discharged by the dispensing pump 5 into the probe 3.

The amplifying circuit 12 amplifies the pressure signal (analogue) output from the pressure sensor 7 and outputs the amplified pressure signal to the presence determining unit 13.

The presence determining unit 13 includes a processor 13a, the detector 13b, a calculator 13c, a determining unit 13d, and a control unit 13e, and a computer device is employed, for example.

The processor 13a serves as a part which performs a processing of converting the pressure signal (analogue) input from the amplifying circuit 12 into a digital signal, and an A/D converter is employed, for example. The detector 13b detects the pressure in the duct 2 from the pressure signal converted by the processor 13a into the digital signal. The calculator 13c calculates the number of mountain pulses in the pressure transition waveform based on the pressure transition detected by the detector 13b, and outputs the calculation result to the determining unit 13d. The determining unit 13d determines the presence of a bubble in the duct 2 based on the number of mountain pulses calculated by the calculator 13c. The control unit 13e controls operations of the nozzle driving unit 4, the pump driving unit 6, the cleansing water pump 8, and the electromagnetic valve 9. The determining unit 13d may make a display device display the determination result or make an alarm device set off a warning sound, to notify an operator.

The dispensing apparatus 1 configured as described above is used in a way to be described below. First, the dispensing pump 5 is driven after the electromagnetic valve 9 is closed to discharge the cleansing water 11 from the probe 3 whose inside has been cleaned (inside cleansing) with the cleansing water 11 into a cleansing vessel.

Here, W1 denotes a waveform at a time of performing the inside cleansing and W2 denotes a waveform at a time of discharging the cleansing water 11 in a pressure transition waveform W shown in FIG. 2. While an output voltage of the pressure sensor 7 is negative and shows a downward convex waveform, the pressure in the duct 2 is a positive pressure in the case of discharging. On the other hand, while an output voltage of the pressure sensor 7 is positive and shows an upward convex waveform, the pressure in the duct 2 is a negative pressure in the pressure transition waveform W in the case of absorbing.

Next, the dispensing pump 5 is driven in the reverse direction to absorb a predetermined amount of air into a tip of the probe 3 (see a waveform W3 in FIG. 2).

Next, the probe 3 is lowered by the nozzle driving unit 4 to make a predetermined amount of the tip of the probe 3 sink in the specimen in the conveyed sample cup 20.

After that, the dispensing pump 5 is driven to absorb a predetermined amount of specimen into the probe 3 (see a waveform W4 in FIG. 2). On this occasion, the specimen is never mixed with the cleansing water 11 since the specimen is absorbed in a state where the air intervenes between the specimen and the cleansing water 11. In addition, the probe 3 absorbs the specimen in an amount slightly larger than the amount necessary for an analysis.

Next, the absorbed specimen is slightly discharged into the sample cup 20 (see a waveform W5 in FIG. 2). Then, the probe 3 is raised by the nozzle driving unit 4 and again lowered by the nozzle driving unit 4 to discharge the absorbed specimen into the reaction vessel which is conveyed by following the sample cup 20 (see a waveform W6 in FIG. 2).

After the probe 3 is again raised by the nozzle driving unit 4, the probe 3 is lowered into the cleansing vessel which is conveyed by following the reaction vessel and the electromagnetic valve 9 is switched to "open". Then, the cleansing water pump 8 is driven, and the cleansing water 11 in the tank 10 is transported into the duct 2 with pressure and discharged into the cleansing vessel from the probe 3 to clean the probe 3 with the cleansing water 11. In this manner, a series of dispensing operation in which one specimen is dispensed from the sample cup 20 into the reaction vessel is completed. On this occasion, when the inside cleansing of the probe 3 with the cleansing water 11 is not sufficient, the probe 3 is sometimes cleaned additionally with a detergent. Besides, when another specimen is supposed to be dispensed, the operation described above is repeated to sequentially dispense a new specimen from a new sample cup 20 into a new reaction vessel.

Here, a left side vertical scale is an output voltage (V) of a pressure signal output from the pressure sensor 7 and a horizontal scale is a time period (sec.) in the pressure transition waveform W shown in FIG. 2. Besides, a signal waveform S shows a waveform of a driving signal, for driving the dispensing pump 5, output from the control unit 13e to the pump driving unit 6, and a right side scale is a driving voltage (V) in FIG. 2.

Figure 3:
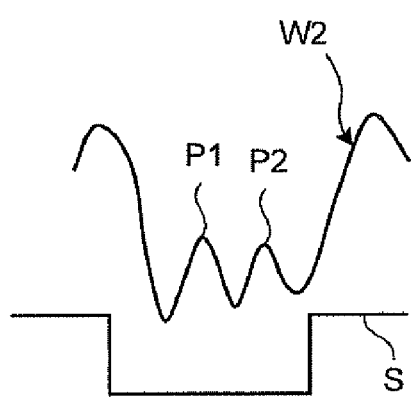
FIG. 3 is a magnified view of a waveform at a time of discharging cleansing water from the probe to a cleansing vessel, showing a case where no bubble is present in a liquid filling a duct.

At this moment, as far as the waveform W2 at the time of discharging the cleansing water 11 from the probe 3 into the cleansing vessel is observed in the pressure transition waveform W for example, when no bubble is present in the cleansing water 11 in the duct 2, a plurality of mountain pulses P1 and P2 can be recognized during a period after the driving signal S is input to the pump driving unit 6 until the input of the driving signal S is stopped, as shown in FIG. 3. where the waveform W2 is magnified. Here, FIGS. 3 to 7 schematically show a part of the signal waveform S and the waveform W2.

Figure 4:
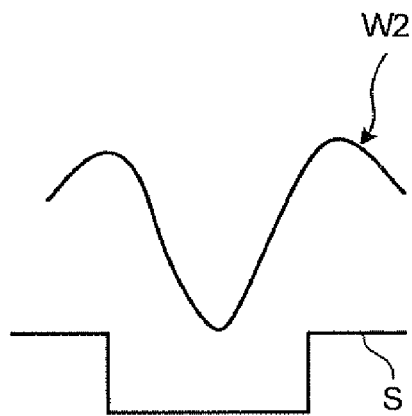
FIG. 4 shows a case where an amount of bubble present in the liquid filling the duct is large compared to the case shown in FIG. 3.

In contrast, when a bubble is present in the cleansing water 11, the pressure transition becomes inactive since a transmission of the pressure becomes slow due to the bubble. Therefore, no mountain pulse is recognized in the waveform W2 as shown in FIG. 4. Here, FIG. 4 shows a case where an amount of the bubble present in the cleansing water 11 is large, and a mountain pulse comes to appear as the amount of the bubble becomes smaller.

Figure 5:
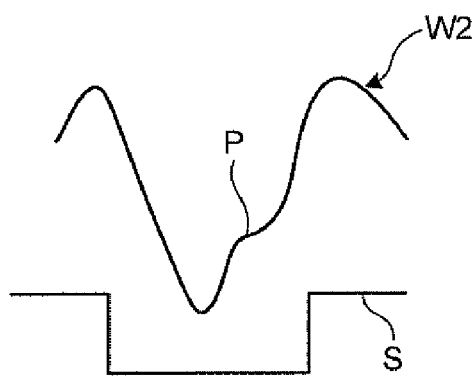
FIG. 5 shows a case where an amount of bubble present in the liquid filling the duct is smaller than that of the case shown in FIG. 4.
Figure 6:
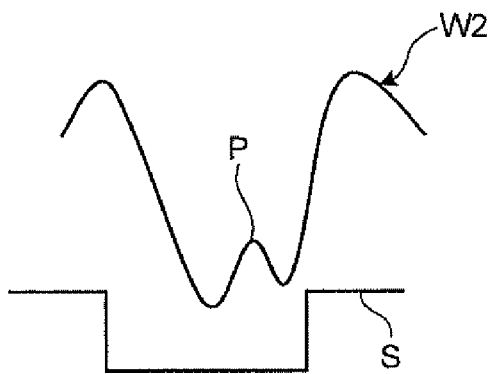
FIG. 6 shows a case where an amount of bubble present in the liquid filling the duct is smaller than that of the case shown in FIG. 5.

When the amount of the bubble present in the cleansing water 11 is moderate enough to be less than the case of FIG. 4, a mountain pulse P slightly appears as shown in FIG. 5. Furthermore, when the amount of the bubble present in the cleansing water 11 is least enough to be even smaller than the case of FIG. 5, the mountain pulse P clearly appears as shown in FIG. 6.

Figure 7:
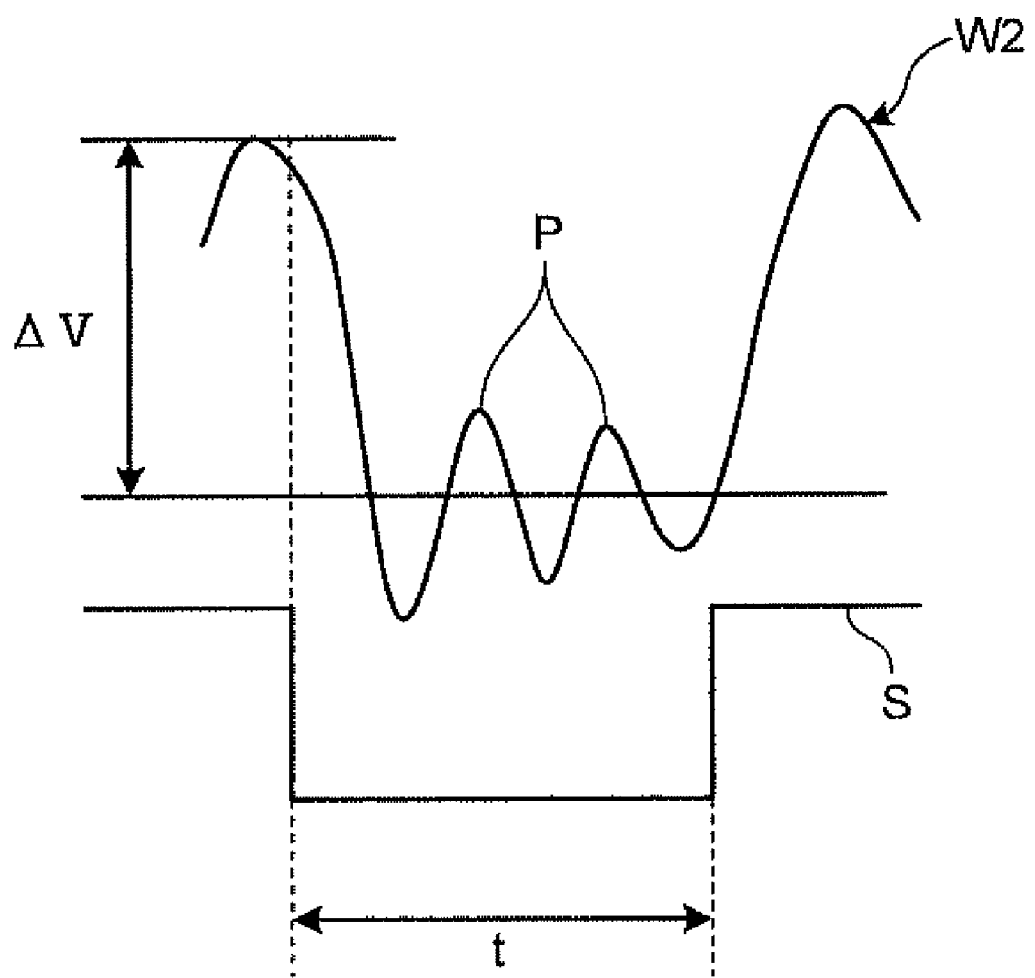
FIG. 7 is an explanatory view showing a method of calculating the number of mountain pulses in the pressure transition waveform based on a detected pressure transition.

Thus, the presence of a bubble in the liquid filling the duct is determined based on the number of mountain pulses in the present invention. More specifically, a voltage value smaller, by a predetermined value $\Delta V$ (=4V), than the voltage value at a time when the driving signal S is input in a signal output time period t which is after the driving signal S is input to the pump driving unit 6 and until the input of the driving signal S is stopped, is set as a threshold value Ts and stored by the determining unit 13d, as shown in FIG. 7. The calculator 13c calculates Ni which is the number of mountain pulses P each having a voltage value exceeding the threshold value Ts in the waveform W2 during the signal output time period t. Besides, the calculator 13c similarly calculates N0 which is the number of mountain pulses P even when the cleansing water 11 in which no bubble is present is discharged. The determining unit 13d compares the numbers Ni and N0 of the mountain pulses P calculated by the calculator 13c, and determines that a bubble is present in the duct 2 when the number Ni is smaller than the number N0 (Ni<N0).

Figure 8:
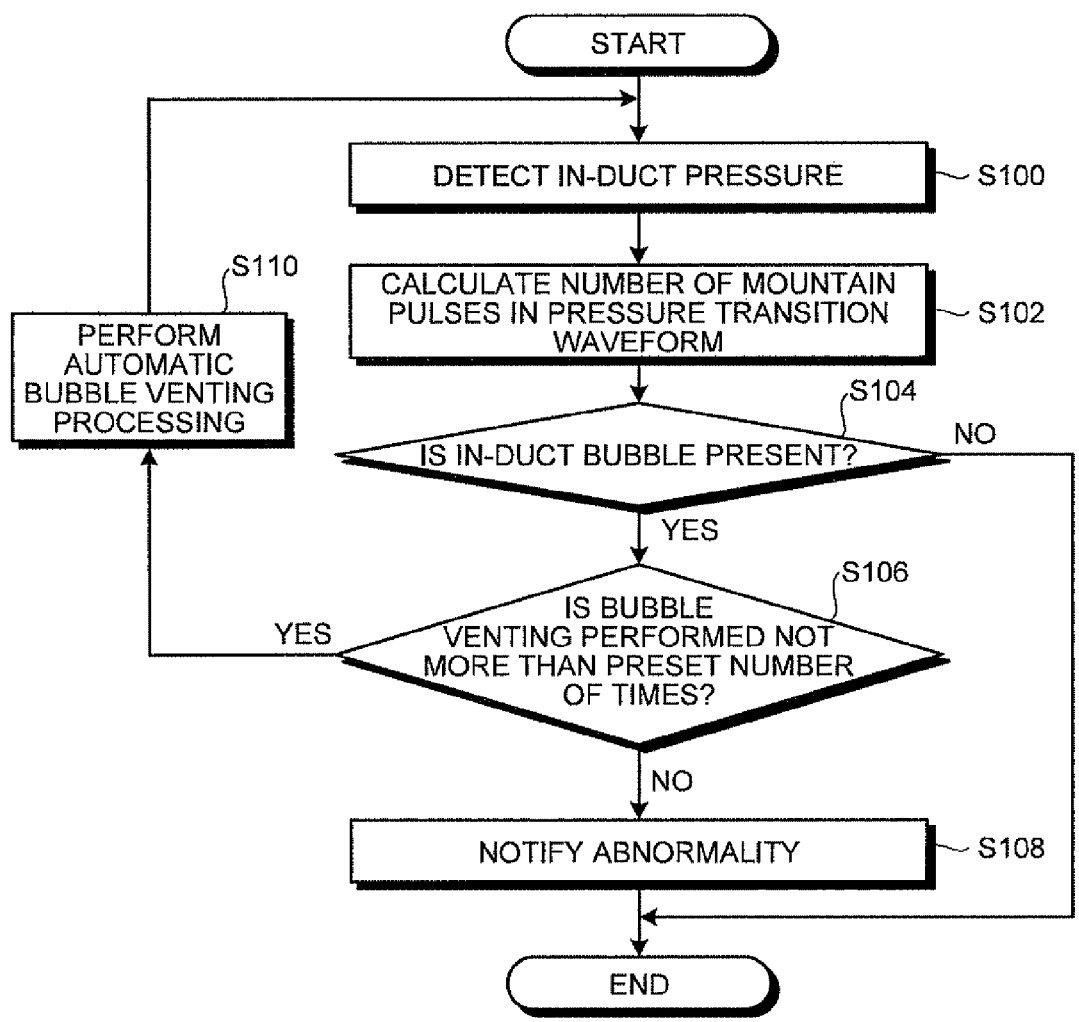
FIG. 8 is a flow chart showing an in-duct bubble presence determining method according to the present invention and a response based on a result of the determination.

A determination, performed by the presence determining unit 13, of the presence of a bubble in the duct 2 and a response based on the determination result will be explained below with reference to a flow chart shown in FIG. 8. First, for example on an occasion of a check performed before starting the dispensing when the analyzing device is switched on to start up, the dispensing apparatus 1 under the control of the control unit 13e drives the dispensing pump 5 and discharges the cleansing water 11 from the probe 3 whose inside has been cleaned (inside cleansing) into the cleansing vessel. Accordingly, the detector 13b detects the pressure in the duct 2 based on the signal output from the pressure sensor 7 to the presence determining unit 13 via the amplifying circuit 12 (step S100).

Next, the calculator 13c calculates the number Ni of mountain pulses in the pressure transition waveform from the pressure detected by the detector 13b based on the threshold value (step S102). Then, the determining unit 13d compares the calculated numbers Ni and N0 of the mountain pulses and determines whether a bubble is present in the duct 2 or not (step S104).

When the number of mountain pulses Ni is more than the number of mountain pulses N0 ("No" at step S104), the determining unit 13d determines that no bubble is present in the duct 2 and ends the determining operation. In this case, the determining unit 13d may display the effect on a display. The dispensing apparatus 1 starts dispensing the liquid sample in response to the end of the determining operation. On the other hand, when the number of mountain pulses Ni is not more than the number of mountain pulses N0 ("Yes" at step S104), the determining unit 13d determines that a bubble is mixed in the duct.

After that, the determining unit 13d determines whether a number of times of a bubble venting is not more than a preset number of times or not (step S106). When the number of times of the bubble venting is more than the preset number of times ("No" at step S106), since the case is such that a bubble is mixed in the duct 2 in spite of the bubble venting operation, the determining unit 13d notifies an abnormality (step S108). As the notification of the abnormality, the effect that a bubble is mixed is displayed on a display device or a warning sound is set off by an alarm, for example.

On the other hand, when the number of times of the bubble venting is not more than the preset number of times ("Yes" at step S106), the determining unit 13d determines that the bubble venting operation is not sufficient and performs an automatic bubble venting processing (step S110). This automatic bubble venting processing is performed by outputting a control signal to the electromagnetic valve 9 to open the valve and driving the cleansing water pump 8 to transport the cleansing water 11 in the tank 10 into the duct 2 with pressure. By this, a bubble mixed in the duct 2 is discharged into the cleansing vessel together with the cleansing water. Thereafter, the determining unit 13d returns to step S100 and repeats the determination on the presence of a bubble in the duct 2.

As described, in the dispensing apparatus and the in-duct bubble presence determining method in the dispensing apparatus according to the present invention, the presence of a bubble in the liquid filling the duct 2 can be determined easily at any time since it is only necessary to detect the pressure transition in the duct 2 by closing the electromagnetic valve 9, driving the dispensing pump 5, and discharging the cleansing water 11 from the probe 3. This is why the dispensing apparatus and the induct bubble presence determining method in the dispensing apparatus according to the present invention do not waste a liquid sample including a specimen or a reagent, and can reduce the time for performing a reexamination.

Here, in a case where the dispensing is restarted after a maintenance of the dispensing apparatus has been performed or after the dispensing operation has been stopped over a long time, it is conceivable that a bubble may arise due to an ambient temperature, an atmospheric pressure, a minute leakage, and the like. Therefore, the determination of the presence of a bubble may also be performed in such a case.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-duct bubble presence determining method in a dispensing apparatus comprising a dispensing nozzle, a duct, a pressure sensor, and a presence determining unit, which performs dispensing by filling the duct to which the dispensing nozzle is connected with a liquid, making the liquid move in the duct to absorb a liquid sample including one of a specimen and a reagent through the dispensing nozzle, and discharging the absorbed liquid sample, comprising the steps of:

the dispensing nozzle discharging the liquid in the duct;
the pressure sensor detecting a transition of a pressure in the duct at the time of the discharge;
the presence determining unit calculating a number of pulses in a pressure transition waveform based on the detected pressure transition; and
the presence determining unit determining a presence of a bubble in the liquid filling the duct based on the calculated number of pulses.

2. The in-duct bubble presence determining method in the dispensing apparatus according to claim 1, wherein when the number of pulses which exceed a predetermined threshold value is not more than one, it is determined that the bubble is present in the liquid filling the duct in the step of determining the presence of the bubble.

3. A dispensing apparatus which determines the presence of an in-duct bubble and performs dispensing by filling a duct to which a dispensing nozzle is connected with a liquid, making the liquid move in the duct to absorb a liquid sample including one of a specimen and a reagent through the dispensing nozzle, and discharging the absorbed liquid sample, comprising:

the duct; and
the dispensing nozzle that discharges the liquid in the duct;
a pressure sensor that detects a transition of a pressure in the duct at the time of the discharge; and
a presence determining unit 13 that calculates a number of pulses in a pressure transition waveform based on the pressure transition in the duct detected by the pressure sensor, and determines a presence of a bubble in the liquid filling the duct based on the calculated number of pulses.

4. The dispensing apparatus according to claim 3, wherein the presence determining unit 13 is configured to determine that the bubble is present in the liquid filling the duct when the number of pulses which exceed the predetermined threshold value is not more than one.

* * * * *